United States Patent [19]

Boesch

[11] 4,076,824
[45] Feb. 28, 1978

[54] ANTHELMINTIC OXADIAZOLINONE DERIVATIVES

[75] Inventor: Roger Boesch, Vitry-sur-Seine, France

[73] Assignee: Rhone-Poulenc Industries, Paris, France

[21] Appl. No.: 654,587

[22] Filed: Feb. 2, 1976

[30] Foreign Application Priority Data

Feb. 3, 1975   France ................................. 75 03281
Feb. 3, 1975   France ................................. 75 03282

[51] Int. Cl.² ............................................. A61K 31/42
[52] U.S. Cl. ................................ 424/272; 260/307 G
[58] Field of Search ..................... 424/272; 260/307 G

[56] References Cited

FOREIGN PATENT DOCUMENTS 4,858,140  11/1971  Japan.

OTHER PUBLICATIONS

Chemical Abstracts, vol. 78 (1973), pp. 72157q and 72162n.

*Primary Examiner*—V. D. Turner
*Attorney, Agent, or Firm*—Stevens, Davis, Miller & Mosher

[57] ABSTRACT

Oxadiazolinone derivatives of the formula:

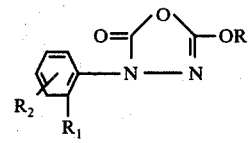

wherein R represents alkyl of 1 through 4 carbon atoms, $R_1$ represents halogen, alkyl of 1 through 4 carbon atoms, alkoxy of 1 through 4 carbon atoms or alkylthio of 1 through 4 carbon atoms, and $R_2$ represents hydrogen, halogen, alkyl of 1 through 4 carbon atoms, alkoxy of 1 through 4 carbon atoms or alkylthio of 1 through 4 carbon atoms, are useful as anthelmintics.

14 Claims, No Drawings

ANTHELMINTIC OXADIAZOLINONE DERIVATIVES

THIS INVENTION relates to oxadiazolinone derivatives.

It is known from the Specification of Japanese Patent Application No. 46-95265 (Publication No. 48-58140) filed by Mitsui Toatsu Co. on Nov. 29 1971 that oxadiazolinone derivatives of the general formula:

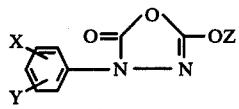

wherein Z represents a lower alkyl radical or a phenyl radical and X and Y each represent a hydrogen or halogen atom or a methyl radical, for example 5-methoxy-3-phenyl-1,3,4-oxadiazolin-2-one, 5-ethoxy-3-(2-methylphenyl)-1,3,4-oxadiazolin-2-one, 5-ethoxy-3-(2,4-dichlorophenyl)-1,3,4-oxadiazolin-2-one and 5-phenoxy-3-phenyl-1,3,4-oxadiazolin-2-one, possess insecticidal and acaricidal properties.

It is also known from the Specification of British Pat. No. 989,627 granted to Farbwerke Hoechst Akt. on an application filed on July 20, 1961, that compounds of general formula I in which the phenyl radical is unsubstituted, or is substituted on one or two of the carbon atoms by a halogen atom or an alkyl or alkoxy group having 1 to 4 carbon atoms, for example 5-ethoxy-3-phenyl-1,3,4-oxadiazolin-2-one, are useful as starting materials for the preparation of therapeutically active triazolidines, which possess blood pressure lowering properties and also exhibit antiphlogistic, analgesic and vasodilatory actions.

It has now unexpectedly been found after extensive research and experimentation that oxadiazolinone derivatives of the general formula:

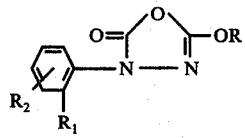

wherein R represents an alkyl radical containing 1 to 4 carbon atoms, $R_1$ represents a halogen (e.g. chlorine, bromine or iodine) atom, or an alkyl, alkoxy or alkylthio radical, such radicals each containing 1 to 4 carbon atoms, and $R_2$ represents a hydrogen or halogen (preferably chlorine) atom, or an alkyl, alkoxy or alkylthio radical, such radicals each containing 1 to 4 carbon atoms, possess anthelmintic properties. When $R_2$ is other than a hydrogen atom, the substituent represented by that symbol may be the same as the substituent in the phenyl radical represented by $R_1$ or different therefrom.

The oxadiazolinone derivatives of general formula II have proved particularly active against experimental infestations of sheep with *Haemonchus contortus, Trichostrongylus axei, Ostertagia circumcincta, Trichostrongylus colubriformis* and *Nematodirus spathiger*, when administered orally at doses of about 25 mg./kg. animal body weight as well as against experimental infestations of dogs with *Ankylostoma caninum* and *Ucinaria stenocephala*, when administered orally at doses of between 6 and 50 mg./kg. animal body weight.

In vitro, the oxadiazolinones of general formula II have proved active against the larvae of digestive strongyles of horses (*Strongylus equinus* and *Trichonema* sp.) at a concentration of between 1/10,000 and 1/30,000.

the oxadiazolinones of general formula II which are particularly active against experimental infestations of sheep, as mentioned above, are those wherein R represents an alkyl radical containing 1, 2 or 3 carbon atoms, $R_1$ represents a halogen atom and $R_2$ represents a hydrogen or halogen atom, and more especially those compounds wherein $R_2$ represents a hydrogen or chlorine atom.

The oxadiazolinones of general formula II which are particularly active against experimental infestations of dogs, as mentioned above, are those wherein R represents a methyl or ethyl radical, and $R_1$ represents a methyl, ethyl, methoxy, ethoxy, methylthio or ethylthio radical, and $R_2$ represents a hydrogen or halogen atom or a methyl or ethyl radical, or $R_1$ represents a halogen atom and $R_2$ represents a methoxy or ethoxy radical, and more especially those compounds wherein R represents a methyl or ethyl radical, and $R_1$ represents a methyl, methoxy, methylthio or ethylthio radical and $R_2$ represents a hydrogen or chlorine atom or a methyl radical, or $R_1$ represents a chlorine atom and $R_2$ represents a methoxy radical.

The following compounds of general formula II are of outstanding interest as anthelmintics:- 3-(2,3-dichlorophenyl)-5-methoxy-1,3,4-oxadiazolin-2-one, 3-(2-bromophenyl)-5-ethoxy-1,3,4-oxadiazolin-2-one, 3-(2-bromophenyl)-5-methoxy-1,3,4-oxadiazolin-2-one, 3-(2-chlorophenyl)-5-methoxy-1,3,4-oxadiazolin-2-one, 3-(2-chlorophenyl)-5-ethoxy-1,3,4-oxadiazolin-2-one, 3-(2-chloro-3-methoxyphenyl)-5-ethoxy-1,3,4-oxadiazolin-2-one, 3-(2-chloro-3-methoxyphenyl)-5-methoxy-1,3,4-oxadiazolin-2-one and 5-methoxy-3-(2-methylthiophenyl)-1,3,4-oxadiazolin-2-one.

The oxadiazolinones of general formula II can also be used for the treatment of helminth infections in man, for example infections of anguillulae and ancylostomes.

According to the present invention, there is provided a method for the treatment of helminth infections in man and in domestic animals (e.g. cattle, sheep, goats, equines, pigs and poultry), for example infections of the gastro-intestinal tract caused by parasitic nematode worms, for example members of the family *Trichostrongylidae*, which comprises the administration of an anthelmintically effective amount of at least one oxadiazolinone derivative of general formula II.

The quantity of the oxadiazolinone administered in the treatment of helminthiases will vary with the species of animal treated, the nature and degree of the infestation, the length of treatment, the method of administration, and the age and weight of the animal. The veterinarian or doctor will determine the posology, taking into account such, and all other, factors.

In veterinary medicine, the oxadiazolinones of general formula II can be used for the treatment of helminthiases caused by nematodes in cattle, sheep, goats and domestic animals in general, at single doses of between 10 and 80 mg./kg. animal body weight administered orally, as well as for the elimination of gastrointestinal strongyles in sheep and intestinal nematodes in dogs.

In human medicine, the oxadiazolinones of general formula II can be used for eliminating anguillulae and ancylostomes at single doses of between 10 and 50 mg./kg. body weight administered orally. These doses can be repeated at regular intervals of several days or several weeks in order to achieve the ultimate elimination of the parasite.

The oxadiazolinones of general formula II are conveniently administered as anthelimintics in the form of compositions in a unit dosage form, and the present invention includes within its scope therapeutically-useful, more especially veterinary, compositions which comprise, as active ingredient, at least one oxadiazolinone derivative of formula II in association with a significant amount of a pharmaceutically-acceptable carrier or coating. The invention includes especially such compositions made up for oral administration, for example a tablet, pill, capsule or bolus, or more particularly, a paste, gel or drench.

Solid compositions for oral administration include compressed tablets, pills, boluses, granules and dispersible powders. In such solid compositions one or more of the active compounds is or are admixed with at least one inert diluent such as potato starch, alginic acid, sucrose, lactose, or a resin. The compositions may also comprise, as is normal practice, additional substances other than inert diluents, e.g. lubricating agents such as magnesium stearate. Semi-solid compositions for oral administration include pastes and gels containing the active substance and a suitable inert diluent such as polyethylene glycol (6000). Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise compatible adjuvants such as wetting, suspending and emulsifying agents and stabilising, thickening, perfuming, sweetening and flavouring agents. The compositions according to the invention for oral administration also include capsules of absorbable material such as gelatin containing one or more of the active substances with or without the addition of diluents or excipients.

Preparations according to the invention for parenteral administration include sterile aqueous, aqueous organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents. They may be sterilised, for example, by filtration through a bacteria-retaining filter, by incorporation in the compositions of sterilising agents, or by heating. They may also be manufactured in the form of sterile solid compositions, which can be dissolved in sterile water or some other sterile injectable medium immediately before use.

The percentage of the oxadiazolinone derivatives of formula II in the above compositions may be varied, it being necessary that it should constitute a proportion such that a suitable dosage for the therapeutic effect desired shall be obtained.

For therapeutic purposes, particularly when continuous administration over a period is desired, the compounds of general formula II may be administered dispersed in, or mixed with, animal feedstuffs, drinking water and other liquids normally consumed by the animals, or in compositions containing the oxadiazolinone derivatives dispersed in or mixed with any other suitable inert physiologically innocuous carrier or diluent which is orally administrable. By the term inert physiologically innocuous carrier of diluent' is meant a carrier or diluent which is substantially non-reactive with the active ingredient and is not harmful to the animals on oral administration. Such compositions may be administered in the form of powders, pellets, solutions, suspensions and emulsions, to the animals to supply the desired dosage of the oxadiazolinone derivatives or used as concentrates or supplements to be diluted with additional carrier, feedstuff, drinking water or other liquids normally consumed by the animals, before administration. Suitable inert physiologically innocuous carriers or diluents include wheat flour or meal, maize gluten, lactose, glucose, sucrose, talc, kaolin, calcium phosphate, potassium sulphate and diatomaceous earths such as kieseliguhr. Concentrates or supplements intended for incorporation into drinking water or other liquids normally consumed by the animals to give solutions, emulsions or stable suspensions, may also comprise the active ingredient in association with a surface-active wetting, dispersing or emulsifying agent such as Teepol, polyoxyethylene(20) sorbitan mono-oleate or the condensation product of β-naphthalenesulphonic acid with formaldehyde, with or without a physiologically innocuous, preferably water-soluble, carrier or diluent, for example, sucrose, glucose or an inorganic salt such as potassium sulphate, or concentrates or supplements in the form of stable dispersions or solutions obtained by mixing the aforesaid concentrates or supplements with water or some other suitable physiologically innocuous inert liquid carrier or diluent, or mixtures thereof.

The compositions described above may be prepared by mixing the oxadiazolinone derivatives of formula II with the inert physiologically innocuous carriers or diluents in any manner known to the art. Solid compositions are conveniently prepared by intimately mixing or dispersing the oxadiazolinone derivatives uniformly throughout the feedstuffs or other solid carrier or diluent by methods such as grinding, stirring, milling or tumbling or by dissolving the oxadiazolinone derivatives in a solvent, e.g. water or a suitable organic solvent, dispersing the solution so obtained in the feedstuff or other solid carrier or diluent and removing the solvent by any means known to the art. Medicated feedstuffs may also be prepared by mixing in concentrates or supplements containing higher concentrates of active ingredient to give feedstuffs throughout which the oxadiazolinone derivatives are uniformly distributed at the desired concentration. The desired concentration of active ingredient in the compositions of the present invention is obtained by the selection of an appropriate ratio of the oxadiazolinone derivative to carrier or diluent.

Medicated animal feedstuffs and compositions containing the oxadiazolinone derivatives of formula II dispersed in, or admixed with, any other suitable inert carrier or diluent, as hereinbefore described, including concentrates or supplements, form a further feature of the present invention.

The oxadiazolinone derivatives conforming to general formula II referred to hereafter in Examples 3 and 4 and the list of compounds thereafter are all new compounds and as such [except for 5-methoxy-3-(2-methoxyphenyl)-, 5-methoxy-3-(2-methylthiophenyl)- and 3-(2-ethylthiophenyl)-5-methoxy-1,3,4-oxadiazolin-2-one] constitute features of the invention.

The oxadiazolinone derivatives of general formula II, wherein R, $R_1$ and $R_2$ are as hereinbefore defined, can all be obtained by the action of phosgene of a compound of the general formula:

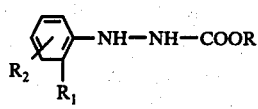   III (wherein R, R₁ and R₂ are as hereinbefore defined), followed by the cyclisation, in a basic medium, of the intermediate compound obtained of the general formula:

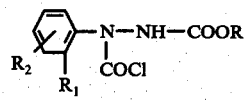   IV wherein R, R₁ and R₂ are as hereinbefore defined.

The reaction with phosgene is generally carried out by heating the reactants in an organic solvent, for example toluene, at the reflux temperature of the reaction mixture.

The cyclisation of the intermediate product of general formula IV is carried out in the presence of a base, such as triethylamine, sodium hydroxide or ammonia, in an organic solvent, for example methylene chloride.

The compounds of general formula III can be prepared by reacting a chloroformate of the general formula:

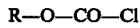   R—O—CO—Cl   V (wherein R is as hereinbefore defined) with a phenylhydrazine of the general formula:

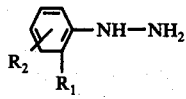   VI wherin R₁ and R₂ are as hereinbefore defined. The reaction is generally carried out in a solvent such as pyridine.

The following Examples illustrate therapeutic compositions according to the invention.

EXAMPLE 1

Tablets having the following composition are prepared in accordance with the usual technique:

| | |
|---|---|
| 3-(2-bromophenyl)-5-ethoxy-1,3,4-oxadiozolin-2-one | 0.500 g. |
| wheat starch | 0.150 g. |
| colloidal silica | 0.040 g. |
| magnesium stearate | 0.010 g. |

EXAMPLE 2

Tablets having the following composition are prepared in accordance with the usual technique:

| | |
|---|---|
| 3-(2-chloro-3-methoxyphenyl)-5-ethoxy-1,3,4-oxadiazolin-2-one | 0.500 g. |
| wheat starch | 0.150 g. |
| colloidal silica | 0.040 g. |
| magnesium stearate | 0.010 g. |

The following Examples illustrate the preparation of new oxadiazolinone derivatives of general formula II.

EXAMPLE 3

Ethyl 3-(2-chlorophenyl)-carbazate (15.2 g.) is added to a 14.8% (w/v) solution (71 cc.) of phosgene in toluene. The solution obtained is then heated gradually until gas ceased to be evolved, whilst condensing the condensable vapours by means of a condenser containing solid carbon dioxide. The temperature of the reaction mixture is then 105° C. The condenser containing solid carbon dioxide is replaced by a coil condenser and the mixture is heated under reflux until the evolution of gas is complete. After cooling, the solution is concentrated under reduced pressure (25 mm. Hg) at 50° C. The residue obtained is dissolved in methylene chloride (71 cc.), then triethylamine (9.5 cc.) is added to the solution and the mixture is stirred overnight at 20° C. Water (71 cc.) is then added in order to dissolve the precipitate of triethylamine hydrochloride. The organic phase is decanted and then washed successively with 0.1N hydrochloric acid (50 cc.) and water (100 cc.). After drying over sodium sulphate, the solvent is removed by evaporation under reduced pressure (25 mm.Hg) at 40° C. The residual solid is recrystallised from petroleum ether, b.p. 35°–60° C., (380 cc.) to give 3-(2-chlorophenyl)-5-ethoxy-1,3,4-oxadiazolin-2-one (13.7 g.), melting at 45° C.

The ethyl 3-(2-chlorophenyl)-carbazate (m.p. 80° C.) used as starting material can be prepared by the action of ethyl chloroformate on 2-chlorophenylhydrazine in pyridine.

EXAMPLE 4

Following the procedure of Example 3, but starting with methyl 3-(2-methoxyphenyl)-carbazate (14 g.) and a 14.8% (w/v) solution (71.5 cc.) of phosgene in toluene, methyl 3-(2-methoxyphenyl)-3-chlorocarbonylcarbazate (17 g.), which melts at 139° C., is obtained after concentration of the toluene solution. This product is suspended in a 0.5N solution of sodium hydroxide (132 cc.) and the suspension is stirred for 15 minutes; methylene chloride (100 cc.) is then added thereto. The methylene chloride phase is decanted and washed with water (2×100 cc.).

After drying over sodium sulphate, the solvent is removed by evaporation under reduced pressure (20 mm.Hg) at 50° C. 5-Methoxy-3-(2-methoxyphenyl)-1,3,4-oxadiazolin-2-one (12.8 g.), melting at 79° C. after recrystallisation from ethanol, is thus obtained.

The methyl 3-(2-methoxyphenyl)-carbazate (m.p. 102° C.) used as starting material is prepared by the action of methyl chloroformate on 2-methoxyphenylhydrazine hydrochloride in pyridine.

Following the procedure of Examples 3 and 4 and using suitable starting materials of general formula III, the following products are prepared:

3-(2-chlorophenyl)-5-methoxy-1,3,4-oxadiazolin-2-one, m.p. 63° C., 3-(2,3-dichlorophenyl)-5-methoxy-1,3,4-oxadiazolin-2-one, m.p. 127° C., 3-(2,3-dichlorophenyl)-5-isopropoxy-1,3,4oxadiazolin-2-one, m.p. 66° C., 3-(2,5-dichlorophenyl)-5-ethoxy-1,3,4-oxadiazolin-2-one, m.p. 120° C., 3-(2-bromophenyl)-5-methoxy-1,3,4-oxadiazolin-2-one., m.p. 91° C., 3-(2-bromophenyl)-5-ethoxy-1,3,4-oxadiazolin-2-one, solidification point 37° C.,
3-(2-bromophenyl)-5-isopropoxy-1,3,4-oxadiazolin-2-one, m.p. 66° C.,
3-(2-bromophenyl)-5-propoxy-1,3,4-oxadiazolin-2-one, solidification point 30° C.,
3-(2-iodophenyl)-5-methoxy-1,3,4-oxadiazolin-2-one, m.p. 106° C.,
3-(4-chloro-2-methoxyphenyl)-5-methoxy-1,3,4-oxadiazolin-2-one, m.p. 107° C.,
5-methoxy-3-(2-methylthiopheny)-1,3,4-oxadiazolin-2-one, m.p. 81° C.,
3-(3-chloro-2-methoxyphenyl)-5-ethoxy-1,3,4-oxadiazolin-2-one, m.p. 60° C.,
3-(2-chloro-3-methoxphenyl)-5-ethoxy-1,3,4-oxadiazolin-2-one, m.p. 106° C.,
3-(2-chloro-3-methoxyphenyl)-5-methoxy-1,3,4-oxadiazolin-2-one, m.p. 108° C.,
5-methoxy-3-(2-methoxy-4-methylphenyl)-1,3,4-oxadiazolin-2-one, m.p. 86° C., and
3-(2-ethylthiophenyl)-5-methoxy-1,3,4-oxadiazolin-2one, m.p. 66° C.

In the specification of my co-pending application Ser. No. 651,783, filed Jan. 23, 1976, there are described and claimed inter alia oxadiazolinone derivatives of general formula II wherein R is as hereinbefore defined, $R_2$ represents a hydrogen atom and $R_1$ *represents an alkyl radical containing b* 2 to 4 carbon atoms, an alkoxy radical containing 1 to 4 carbon atoms or an alkylthio radical containing 1 to 4 carbon atoms, which compounds possess insecticidal, acaricidal and nematicidal activities

I claim:

1. A method for the treatment of helminth infections in domestic animals and humans which comprises administering orally to a dometic animal or a human being infected with helminths an anthelmintically effective amount of an oxadiazolinone derivative of the formula:

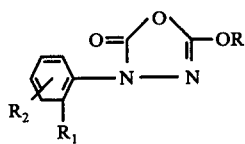

wherein R represents alkyl of 1 through 4 carbon atoms, $R_1$ represents halogen, alkyl of 1 through 4 carbon atoms, alkoxy of 1 through 4 carbon atoms or alkylthio of 1 through 4 carbon atoms, and $R_2$ represents hydrogen, halogen, alkyl of 1 through 4 carbon atoms, alkoxy of 1 through 4 carbon atoms or alkylthio of 1 through 4 carbon atoms.

2. The method according to claim 1 in which the domestic animal is infected with parasitic nematode worms.

3. The method according to claim 1 in which the domestic animals treated are cattle, sheep, goats, equines, pigs, poultry or dogs.

4. The method according to claim 1 in which the domestic animal is given a dose of oxadiazolinone derivative of between 10 and 80 mg./kg. animal body weight.

5. The method according to claim 4 in which the oxadiazolinone derivative is administered orally to sheep to treat infestations of *Haemonchus contortus, Trichostrongylus axei, Ostertagia circumcincta, Trichostrongylus colubriformis* or *Nematodirus spathiger.*

6. The method according to claim 4 in which the oxadiazolinone derivative is administered orally to dogs to treat infestations with *Ankylostoma caninum* or *Ucinaria stenocephala.*

7. The method according to claim 1 for the treatment of helminth infections in sheep wherein the oxadiazolinone derivative employed is a compound of the formula specified in claim 1 wherein R represents alkyl of 1, 2 or 3 carbon atoms, $R_1$ represents halogen and $R_2$ represents hydrogen or halogen.

8. The method according to claim 7 in which $R_2$ represents hydrogen or chlorine.

9. The method according to claim 1 for the treatment of helminth infections in dogs wherein the oxadiazolinone derivative employed is a compound of the formula specified in claim 1 wherein R represents methyl or ethyl, and $R_1$ represents methyl, ethyl, methoxy, ethoxy, methylthio or ethylthio and $R_2$ represents hydrogen, halogen, methyl or ethyl, or $R_1$ represents halogen and $R_2$ represents methoxy or ethoxy.

10. The method according to claim 9 wherein R represents methyl or ethyl, and $R_1$ represents methyl, methoxy, methylthio or ethylthio and $R_2$ represents hydrogen, chlorine or methyl.

11. The method according to claim 9 wherein $R_1$ represents chlorine and $R_2$ represents methoxy.

12. The method according to claim 1 for the treatment of helminth infections in a human being in which the oxadiazolinone derivative is administered orally to a human being at a dose of between 10 and 50 mg./kg. body weight.

13. The method according to claim 12 in which the helminth infection is due to anguillulae or ancylostomes.

14. The method according to claim 1 in which the oxadiazolinone derivative administered to the domestic animal or human being is selected from the group consisting of 3-(2,3-dichlorophenyl)-5-methoxyl-1,3,4-oxadiazolin-2-one, 3-(2-bromophenyl)-5-ethoxy-1,3,4-oxadiazolin-2-one, 3-(2-bromophenyl)-5-methoxy-1,3,4-oxadiazolin-2-one, 3-(2-chlorophenyl)-5-methoxy-1,3,4-oxadiazolin-2-one, 3-(2-chlorophenyl)-5-ethoxy-1,3,4-oxadiazolin-2-one, 3-(2-chloro-3-methoxyphenyl)-5-ethoxy-1, 3,4-oxadiazolin-2-one, 3-(2-chloro-3-methoxyphenyl)-5-methoxy-1,3,4-oxadiazolin-2-one and 5-methoxy-3-(2-methylthiophenyl)-1,3,4-oxadiazolin-2-one.

* * * * *